(12) United States Patent
Loser

(10) Patent No.: US 7,472,444 B2
(45) Date of Patent: Jan. 6, 2009

(54) DEVICE FOR SUPPORT OF THE HEAD

(75) Inventor: Michael Loser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 315 days.

(21) Appl. No.: 11/245,321

(22) Filed: Oct. 5, 2005

(65) Prior Publication Data
US 2006/0083355 A1 Apr. 20, 2006

(30) Foreign Application Priority Data
Oct. 15, 2004 (DE) .................. 10 2004 050 366

(51) Int. Cl.
*A47C 20/00* (2006.01)
(52) U.S. Cl. .................. 5/636; 5/601; 5/622
(58) Field of Classification Search .......... 5/601, 5/621, 622, 636, 637, 640; 378/20, 208, 378/209
See application file for complete search history.

(56) References Cited
U.S. PATENT DOCUMENTS

| | | | | | |
|---|---|---|---|---|---|
| 273,974 | A | * | 3/1883 | Everiss .................. | 5/634 |
| 319,537 | A | * | 6/1885 | Winter .................. | 5/634 |
| 364,051 | A | * | 5/1887 | Sieber .................. | 5/618 |
| 1,515,886 | A | * | 11/1924 | Rumsey .................. | 27/13 |
| 2,614,271 | A | * | 10/1952 | Neil .................. | 5/640 |
| 2,817,857 | A | * | 12/1957 | Hockensmith .................. | 5/640 |
| 3,289,222 | A | * | 12/1966 | Nielsen .................. | 5/617 |
| 3,484,878 | A | * | 12/1969 | Nielsen .................. | 5/617 |
| 5,233,713 | A | * | 8/1993 | Murphy et al. .................. | 5/636 |
| 5,276,927 | A | * | 1/1994 | Day .................. | 5/622 |
| 2002/0184706 | A1 | * | 12/2002 | Riach .................. | 5/632 |
| 2004/0055089 | A1 | * | 3/2004 | Dinkler et al. .................. | 5/622 |

FOREIGN PATENT DOCUMENTS

| | | |
|---|---|---|
| DE | 40 40 789 A1 | 7/1992 |
| DE | 297 06 436 U1 | 7/1997 |
| EP | 1 009 284 B1 | 1/2004 |

* cited by examiner

*Primary Examiner*—Patricia L Engle
*Assistant Examiner*—Gilbert Y Lee
(74) *Attorney, Agent, or Firm*—Schiff Hardin LLP

(57) ABSTRACT

A device for supporting the head of a patient is accommodated on a patient bed of an x-ray apparatus. To prevent image artifacts, the device has a head shell mounted on a fastening part by means of a joint, and a support is provided between the head shell and the fastening part for adjustment of the angle of inclination of the head shell.

8 Claims, 2 Drawing Sheets

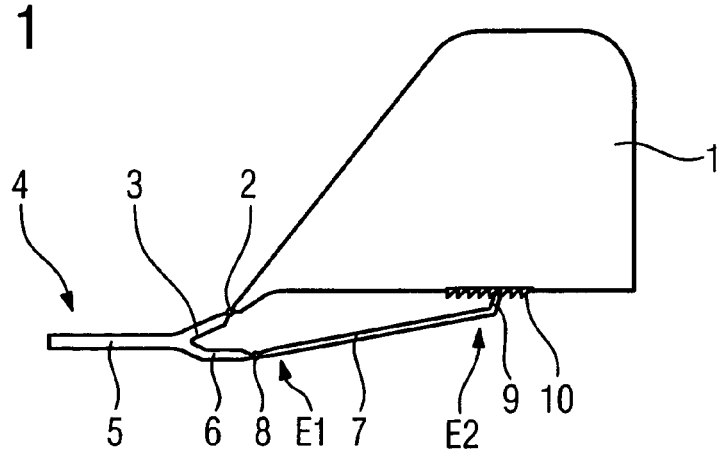
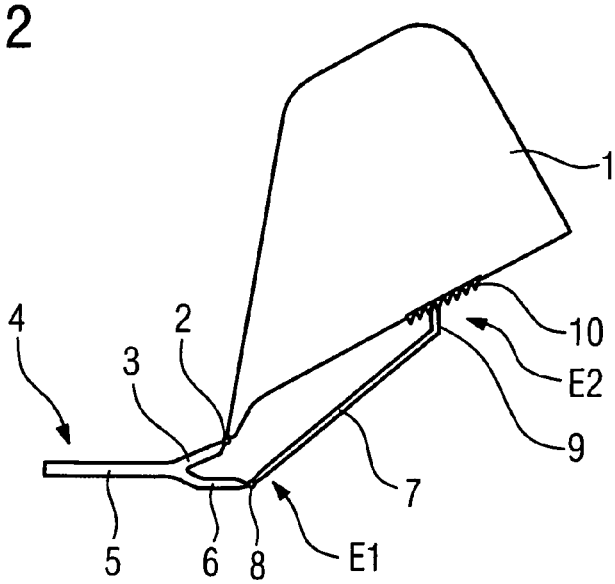
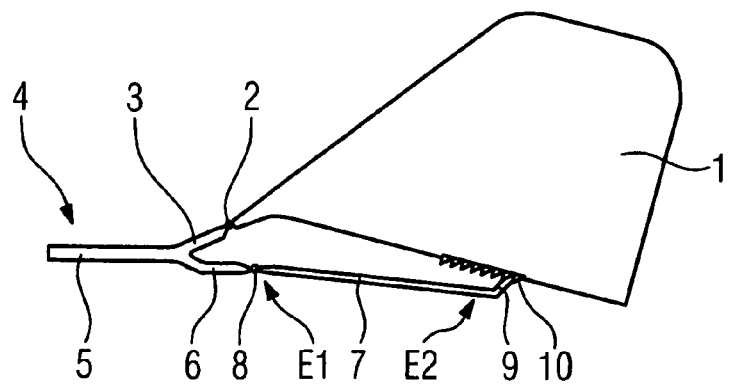

DEVICE FOR SUPPORT OF THE HEAD

BACKGROUND OF THE INVENTION

1. Field of the Invention

The invention concerns a device to support the head of a patient accommodated on a patient bed of an x-ray apparatus.

2. Description of the Prior Art

Conventionally, a head shell that can be affixed to the patient is provided for medical examination of the head, for example by means of x-ray computed tomography. To prevent artifacts in the head image, the head shell is produced from a material permeable for x-rays, for example fiber-reinforced plastic. To adjust the necessary examination position of the head, the angle of inclination of the head shell can be adjusted relative to the patient bed. For this purpose, the head shell is connected with the patient bed via a hinge executed such that it can be locked by a clamping screw. A leg of the hinge is connected with a fastening part to fasten the device to the patient bed. Substantial material thicknesses are required in order to ensure a sufficient stability of the hinge (likewise produced from a material permeable for x-rays). In practice, such a hinge causes image artifacts.

To minimize or prevent such artifacts one known approach, using asymmetrical configuration, is to arrange the hinge as far as possible outside the region of the head to be examined. The head shell is connected, for example, with the patient bed via a laterally mounted arm fashioned in the form of a half-arc, the hinge being a component of the arm. The occurrence of artifacts still can not be completely prevented with this relatively elaborate design. As before, it is necessary to eliminate such artifacts by means of complicated calculational correction methods on the image data after the implementation of a measurement (scan).

DE 297 06 436 U1 discloses a skull supporting device for a patient bed of a computed tomography system. An adapter part that can be attached on the patient bed is provided. A skull support is fastened on a carrier and held on the adapter part on one side by this carrier by means of a carrier arm, and can be pivoted around a horizontal axis. Locking of the skull support is possible by means of a blocking key that engages teeth on the adapter part. The blocking key can transfer the hinge mechanical moment (torque) that occurs upon loading of the skull support to a support part that is affixed on the underside of the carrier of the skull support. The forces arising from the weight of the head are conducted onto the pivotable hinge between the adapter part and carrier arm via the support part and the blocking key. The pivotable hinge must be able to operate under significant mechanical load and therefore must be ruggedly designed, thus requiring relatively massive parts. In tomographical acquisitions in which the x-ray source and detector rotate around the head of the patient, the pivotable connection is located in the beam path and can cause artifacts due to radiation absorption or radiation deflection.

A device for retention of the head in skull surgery is known from DE 40 40 789 A1. The device has a support for the back of the head to support the head of a patient lying on his or her back. With a first part and a second part of a mount, the support for the back of the head is connected with a patient support table by a clampable swivel joint. The swivel joint can be clamped to change the position of the head of the patient. The swivel joint and its clamping device accordingly bear the entire weight of the head and the device for retention of the head. The swivel joint therefore must be fashioned with a high mechanical stability. Low material thicknesses thus cannot be realized. In order to prevent artifacts in the computed tomography image, it is proposed to use polymethylacrylate for many parts of the retention device, but an aluminum alloy is used for the swivel joint. This is not permeable to x-rays. So as to generate as few artifacts as possible in the tomographic image, the hinge is arranged outside of the region of the head to be examined. This means that cantilever forces acting on the swivel joint are even larger and the design is thereby even more elaborate.

A device for supporting a patient in an x-ray examination is known from DE 698 21 368 T2. A tiltable headrest is provided that is connected via a connection piece with a retention plate for supporting the upper body of the patient. A pivotable joint is provided between the connection piece and the headrest. The joint must accommodate forces arising due to the weight of the head. From FIG. 8 it is clear that the joint has teeth and can be clamped. In order to withstand the loads, the joint must be massively designed. The problem of artifact formation is addressed by the joint being arranged above the region of the head to be examined. Nevertheless, artifacts cannot be precluded.

SUMMARY OF THE INVENTION

An object of the present invention is to provide a head support suitable for use in medical imaging systems that avoids the disadvantages of conventional supports. It is a further object to provide such a support that can be produced simply and cost-effectively and with which image artifacts can be prevented in an x-ray examination.

This object is achieved in accordance with the invention by a device having a support for locking of an angle of inclination of the head shell, that is produced from a material permeable to x-rays and that supports the head shell against the fastening part. The fastening part has a fastening section for fastening to the patient bed and a first retention arm extending therefrom. The head shell is mounted on the first retention part such that it can pivot by means of the joint. The fastening part has a second retention arm extending from the fastening section, on which the support is supported. The support is arranged between the head shell and the second retention arm. The fastening part preferably is produced in one piece. The first retention arm and the second retention arm can extend like a fork from the fastening section. The fastening section can be formed, for example, from a plate having at least one aperture for the passage of fastening, elements therethrough, such as screws and the like.

The support bears the largest part of the load of a resting head. Due to the provision of the support, it is possible to construct the joint using lower material thicknesses because the joint itself does not have to be lockable, and only a small part of the forces produced by the weight of the head must be accommodated. The support can likewise be constructed using a low material thickness. Overall, a design results that barely influences the data acquisition in an x-ray computed tomography apparatus. The formation of image artifacts can be nearly completely prevented. A computational correction of the measurement results after the measurement can be foregone. The inventive device, moreover, can be produced relatively simply and cost-effectively.

In an embodiment, the support is mounted such that it can pivot on the second retention arm by means of a further joint. Alternatively, the support can be fashioned to be flexible and extend from the second retention arm. In this case, the support also can be produced as one piece with the fastening part.

In another embodiment, the other end of the support engages in a locking device provided on the underside of the head shell. The locking device can be projections arranged in succession in the longitudinal extension of the head shell, against which projections the other end of the support is braced. Depending on which the projections the other end is braced against, the angle of inclination of the head shell can be adjusted in steps relative to the patient bed. Instead of the projections, apertures (for example slits running transversely to the longitudinal extension of the head shell) can be provided into which the other end of the support can be inserted.

In a further embodiment, the support is pivotably mounted at its other end on the underside of the head shell by means of a further joint. The support can be flexibly fashioned and mounted fixed on the underside of the head shell. In this case, the support also can be produced in a one-piece design with the head shell. The support can engage at one end thereof in a further locking device provided on the second retaining arm. As with the initially-mentioned locking device, the further locking device can be a number of projections disposed in succession or can be apertures that enable bracing of the end of the support, and therewith adjustment of the angle of inclination of the head shell relative to the patient bed.

It has proven to be particularly appropriate for the joint or the further joint to be fashioned as an articulation that is transparent to x-rays. Such an articulation can be, for example, a film articulation that can be reinforced with fibers to increase the lifespan. In contrast to the articulations or joints conventionally used according to the prior art, such an articulation barely interferes with the measurement, for example by means of x-ray computed tomography.

According to a further embodiment, the support is telescopically variable in length. For this purpose, the support can be executed in two parts, one part being a tube and the other part being a threaded rod inserted into this tube. The threaded rod can be adjusted in length relative to the tube by a nut (provided on the threaded rod), but it is also possible for the rod in the tube to be locked, for example by means of a clamping device.

The retaining part, the support and the head shell appropriately exhibit a common plane of symmetry. This means that the retaining part, the support and the head shell are symmetrical. This makes their construction easier.

The head shell, the retaining part and the support can be produced from a fiber-reinforced plastic, preferably reinforced with carbon fibers. Such a material exhibits a particularly high rigidity and can be fashioned particularly thin for construction of the inventive device. The device thus can be made particularly light.

DESCRIPTION OF THE DRAWINGS

FIG. 1 is a side view of a first embodiment of a head support device in accordance with the invention at a tilt angle of 0°.

FIG. 2 shows the device according to FIG. 1 at a tilt angle of 30°.

FIG. 3 shows the device according to FIG. 1 at a tilt angle of −15°.

DESCRIPTION OF THE PREFERRED EMBODIMENTS

Figure 4:
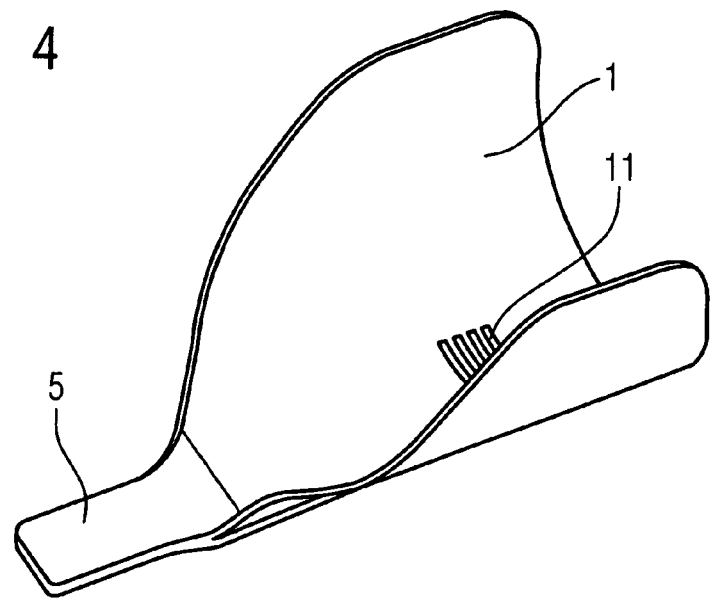
FIG. 4 is a perspective first view of a second embodiment of a head support device in accordance with the invention.

FIG. 1 through 3 show a head shell 1 that is mounted on a first retention arm 3 and is pivotable by means of a first articulation 2. The first retention arm 3 is a component of a general fastening part designated with the reference character 4. The fastening part 4 is essentially composed of the first retention arm 3, a fastening section 5 as well as a second retention arm 6. The fastening part 4 is appropriately produced in a one-piece design made from plastic reinforced with carbon fibers.

A support 7 (preferably rod-like or bar-like) is mounted at one end E1 on the second retention arm 6 via a second articulation 8. The support 7 and/or the articulations 2, 8 is/are produced from a material permeable to x-rays, for example a plastic reinforced with carbon fibers.

The other end E2 of the support 7 has a section 9 that is angled toward the head shell 1, the section 9 engaging in a tooth of a tooth row 10 provided on the underside of the head shell 1. The tooth row 10 is parallel to the longitudinal extent of the head shell 1, such that the angle of inclination of the head shell 1 can be adjusted (by bracing the support 9 in one of the teeth of the tooth row 10) relative to the fastening section 5 provided for fastening on a patient bed (not shown).

FIGS. 2 and 3 show the device according to FIG. 1 with differently-adjusted angles of inclination of 30°-15° relative to the fastening section 5.

Figure 5:
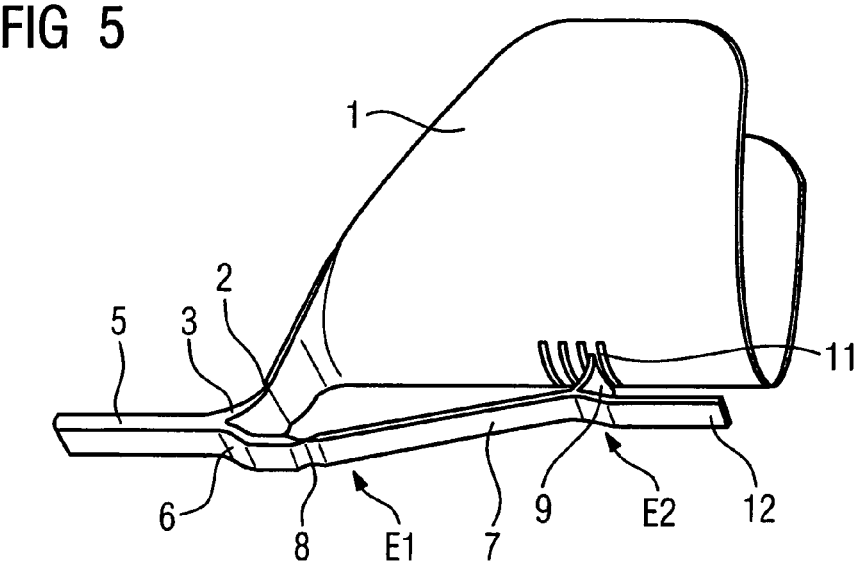
FIG. 5 is a perspective second view of the device according to FIG. 4.

FIGS. 4 and 5 show perspective views of a second exemplary embodiment of the invention. Instead of the tooth row 10, a series of parallel slits 11 is provided on the head shell 1, in which slits 11 a projection (not shown) extending from the angled section 9 engages. Furthermore, a grip 12 extending from the other end E2 can be provided for adjustment of the support 7.

Figure 6:
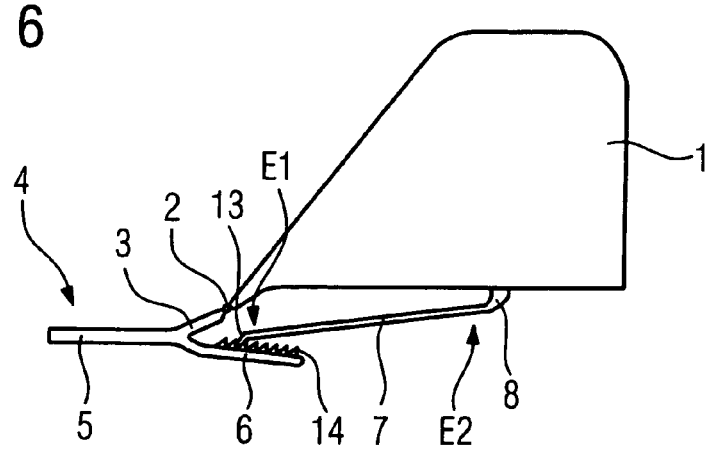
FIG. 6 is a side view of a third embodiment of a head support device in accordance with the invention.

FIG. 6 shows a third exemplary embodiment of the device. The second articulation 8 is provided on the underside of the head shell 1. The end E1 has a further angled section 13 that engages in a further tooth row 14 on the second retention arm 6.

Instead of the further tooth row 14, slits, holes or the like can naturally be provided. Particularly in the variant shown in FIG. 3, it is possible to omit the second articulation. The support 7 alternatively can be mounted fixed on the underside of the head shell 1. In this case the support 7 is made flexible so that it can be curved so that the further angled section 13 can be braced by any tooth of the further tooth row 14.

Instead of the tooth rows 10, 14 or the slit 11, it is naturally also possible to provide other suitable devices with which the support 7 can be locked in different positions. For example, the support 7 can be formed as a threaded rod guided into a tube and with a nut on the threaded rod in order to adjust the length of the support 7. Given a two-part execution of the support 7, clamping or stopping devices can also be provided in order to lock a set length.

Although modifications and changes may be suggested by those skilled in the art, it is the intention of the inventors to embody within the patent warranted heron all changes and modifications as reasonably and properly come within the scope of their contribution to the art.

The invention claimed is:

1. A device supporting the head of a patient accommodated on a patient bed of an x-ray apparatus, comprising:
  a head shell configured to receive and hold the head;
  a one-piece fastening part having a Y-shape;
  a support comprised of material permeable to x-rays disposed to brace said head shell against said one-piece fastening part to set an angle of inclination of said head shell relative to said patient bed;
  said one-piece fastening part comprising a fastening section and a first retention arm and a second retention arm, said first and second retention arms extending from and diverging from said fastening section to form said Y-shape;

said fastening section being configured for immobile fastening to the patient bed;

an articulation that is transparent to x-rays, said articulation pivotably mounting said head shell to said first retention arm; and said support engaging said head shell and said second retention arm and being disposed between said head shell and said second retention arm.

2. A device as claimed in claim 1 wherein said support is comprised of flexible material and projects from said second retention arm.

3. A device as claimed in claim 1 wherein said fastening part and said support and said head shell share a common plane of symmetry.

4. A device as claimed in claim 1 wherein each of said head shell, said one-piece fastening part and said support are comprised of fiber-reinforced material.

5. A device as claimed in claim 4 wherein each of said head shell, said one-piece fastening part and said support are comprised of carbon fiber-reinforced material.

6. A device as claimed in claim 1 wherein said head shell has an underside, and wherein said support is comprised of flexible material and projects from said underside of said head shell.

7. A device as claimed in claim 6 comprising a locking device on said second retention arm engaging another end of said support opposite said one end.

8. A device as claimed in claim 7 wherein said locking device comprises a plurality of receptacles each sized to receive and hold said another end of said support, said head shell being pivoted via said articulation to respectively different angles relative to said one-piece fastening part depending on which said receptacles receives and holds said another end of said support.

* * * * *